United States Patent [19] [11] 4,451,260
Mitra [45] May 29, 1984

[54] SUSTAINED RELEASE ORAL MEDICINAL DELIVERY DEVICE

[75] Inventor: Sumita B. Mitra, Woodbury, Minn.

[73] Assignee: Minnesota Mining and Manufacturing Company, St. Paul, Minn.

[21] Appl. No.: 362,116

[22] Filed: Mar. 26, 1982

[51] Int. Cl.³ .............................................. A61K 9/22
[52] U.S. Cl. ....................................... 604/890; 424/21
[58] Field of Search .............................. 604/890–900; 424/18–22

[56] References Cited

U.S. PATENT DOCUMENTS

| | | | |
|---|---|---|---|
| 3,444,858 | 5/1969 | Russell | 128/260 |
| 3,948,262 | 4/1976 | Zaffaroni | 128/260 |
| 3,976,764 | 8/1976 | Watanabe et al. | 424/19 |
| 4,126,503 | 11/1978 | Gardner | 156/184 |
| 4,136,145 | 1/1979 | Fuchs et al. | 264/164 |
| 4,140,755 | 2/1979 | Sheth et al. | 424/21 |
| 4,167,558 | 9/1979 | Sheth et al. | 424/22 |

OTHER PUBLICATIONS

*Controlled Release Technologies; Methods, Theory, and Applications*, vol. I, editor A. F. Kydonieus, CRC Press Inc., Boca Raton, Florida, pp. 1–14, (1980).
Millipore Corp., Bulletin PB085.

Primary Examiner—Benjamin R. Padgett
Assistant Examiner—T. J. Wallen
Attorney, Agent, or Firm—Donald M. Sell; James A. Smith; Lorraine R. Sherman

[57] ABSTRACT

A flexible, sheet-like, sustained release medicament device for orally administering a predetermined selective dose of a medicament and a method of preparing the device is disclosed. The device is of a multilayer composite construction comprising (a) at least one carrier film comprising at least one water-insoluble polymer and containing medicament, and (b) at least one barrier film overlaying said carrier film on at least one surface thereof and sealed to said carrier film along its periphery and in such a way as to entrap small quantities of air between said carrier and barrier films, said barrier film comprising at least one water-insoluble and water- and medicament-permeable polymer or copolymer, said multilayer composite construction having a bulk density of less than 1.0 g/cc, so as to render the sustained release medicament device buoyant in the gastric juices of the stomach, and being facilely divisible into any desired length.

20 Claims, 6 Drawing Figures

SUSTAINED RELEASE ORAL MEDICINAL DELIVERY DEVICE

DESCRIPTION

1. Technical Field

The present invention relates to a multilayered medicament delivery device of the sustained release type for orally administering a predetermined selective dose of a medicament. In another aspect, it relates to a method of preparing the medicament delivery device of the present invention. In a further aspect, it relates to an apparatus for preparing said delivery device.

2. Background Art

The convenience of administering a single dose of medication which releases an active medicament over an extended period of time so as to achieve a constant rate of release of medicament has long been recognized in the pharmaceutical field. Since oral administration of single dose medicinals is simple and desirable, considerable interest has been expressed in increasing the residence time of medicaments in the stomach.

One way to retain medication in the stomach is to close off the pylorus, the opening from the stomach into the first part of the small intestine, before or during the administration of a drug. Tablets or other drug dispensing devices which swell, inflate, or unfold when in contact with gastric juices and thus become too large to enter the pylorus are known in the art.

Sustained release devices which are buoyant in gastric juices have been disclosed. U.S. Pat. Nos. 4,140,755 and 4,167,558 relate to a sustained release, hydrodynamically balanced hydrocolloid-medicament tablet having a bulk density of less than 1.0 which is capable of floating in gastric fluid. U.S. Pat. No. 3,976,764 teaches a solid therapeutic preparation for gastric diseases, in which an empty globular shell, granular lump, or oval shaped nucleus of polystyrol foam of high buoyancy is coated on the external surface with a medicament and additives. Alternatively the medicament may be within the hard capsule as a disc shaped tablet.

Drug administering vehicles that are divisible into unit dosage forms are taught in U.S. Pat. Nos. 3,444,858, 4,126,503, and 4,136,145.

DISCLOSURE OF THE INVENTION

The present invention provides a flexible, sustained release medicament device for oral administration which: (1) releases medication approaching a zero order release rate, (2) releases medication for a prolonged period of time, (3) remains buoyant in the stomach for an extended period of time during release of medicament, (4) comprises a multilayered polymer film which both controls the rate of release and aids in the buoyancy of the medicament, (5) is in a linear form suitably marked for facile measurement of prescribed medical dosage according to length and capable of being easily cut to the desired length and (6) can be dispensed and administered in a compact form which extends in the stomach to remain buoyant.

The orally administered, sustained release, flexible medicament device of multilayer composite construction is comprised of at least one carrier film and at least one barrier film, the carrier film(s) containing medicament and the barrier film(s) comprising at least one water-insoluble and permeable polymer and additives to control release of medicament. The barrier film(s) is sealed or affixed to the carrier film(s) along its periphery in such a way as to entrap air onto one or more surfaces of the carrier film(s) and render the sustained release medicament device buoyant in the gastric juices of the stomach during release of medication.

Since the ratio of effective dose to toxic dose for some medicinals is very small, e.g. dicoumarin, the sustained release medicament delivery device of the present invention has the desirable property of being capable of fine adjustment to the needs of the recipient. It is capable of being administered in a predetermined selective dose that is not necessarily a unit dose but one that can be accurately measured and dispensed according to linear measurement.

Release of medicament through the barrier and carrier films appears to be achieved by a combination of leaching, diffusion (permeability), and erosion. Initial erosion of the films and subsequent leaching of medicament occurs when the excipient or water soluble plasticizer dissolves in the gastric juices. Permeability depends upon the reservoir concentration (conc. of medicament in the device), membrane thickness, polymer stiffner, co-diffusants, molecular weight of diffusants, and chemical functionality of the transport of active ingredients. For example, varying the thickness and stiffness of the barrier film enables incorporation therein of tailor-made properties for a specific controlled release application. It is desirable that the device maintain its integrity for a period up to several weeks, preferably 4 to 24 hours, before exiting the stomach or degrading.

BRIEF DESCRIPTION OF THE DRAWING

In the accompanying drawing

DETAILED DESCRIPTION OF THE INVENTION

The present invention provides a flexible, sheet-like, sustained release medicament device for orally administering a predetermined selective dose of a medicament, which device is of a multilayer composite construction comprising (a) at least one carrier film comprising at least one water-insoluble polymer and containing medicament, and (b) at least one barrier film overlaying said carrier film on at least one surface thereof and sealed to said carrier film along its periphery and in such a way as to entrap small quantities of air between said carrier and barrier films, said barrier film comprising at least one water-insoluble and water- and medicament-permeable polymer or copolymer and additives to control the release of medicament, said multilayer composite construction having a bulk density of less than 1.0 g/cc and being facilely divisible into any desired length.

As used in this application:

"flexible" means pliant or conforming under stress to a new shape, yet still maintaining its integrity;

"sustained release" means a technique or method in which active chemicals are made available to a specified target at a rate and duration designed to accomplish an intended effect;

"permeable polymer" means one that allows migration or transport of substances, such as water, medicament, excipient, or water-soluble plasticizer therethrough;

"zero order" release rate means a rate of release that is constant;

"medicament" means any composition or substance which will produce a pharmacologic response; and "facilely divisible" means readily and easily subdivided, as for example by cutting with a scissors, into any dosage which is not necessarily a unit dose.

Figure 1:
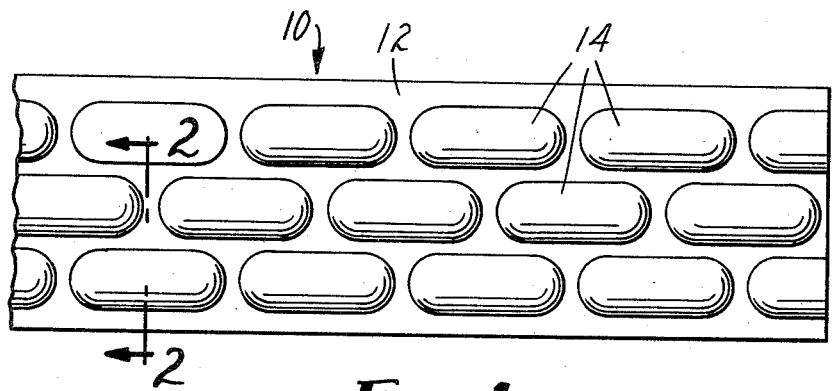
FIG. 1 is a top plan view of a medicament containing device in strip form showing entrapped air pockets.
Figure 2:
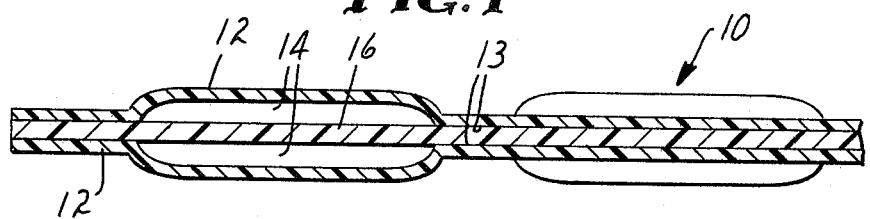
FIG. 2 is an enlarged cross-sectional view of the device of FIG. 1 taken along lines 2—2.

Referring to the accompanying drawing, FIG. 1 shows one embodiment of the multilayered sustained release medicament containing device 10 with outer barrier film 12 enclosing pockets of air 14. FIG. 2 is an enlarged cross-sectional view of device 10 taken along line 2—2 of FIG. 1. Barrier films 12 are shown overlying air pockets 14 and carrier films 16 which has medicament therein. Films 12 and 16 sealably adhere at surfaces 13.

Figure 3:
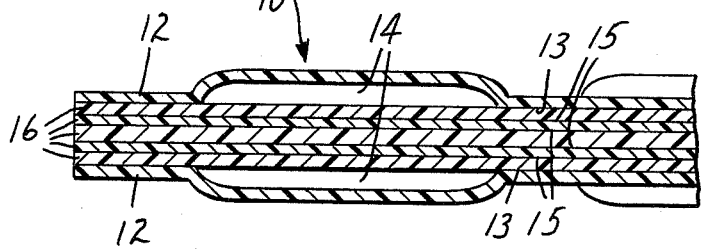
FIG. 3 is an enlarged cross-sectional view of a device similar to that shown in FIG. 2 showing another embodiment of the present invention.

FIG. 3 is an enlarged cross-sectional view of another embodiment of the present invention 10 showing barrier films 12, air pockets 14, and a plurality of carrier films 16, each of which can carry therein the same medicament, different medicaments, or, when desired, no medicament at all. Films 12 and 16 sealably adhere at surfaces 13 and and films 16 adhere to each other at surfaces 15.

Figure 4:
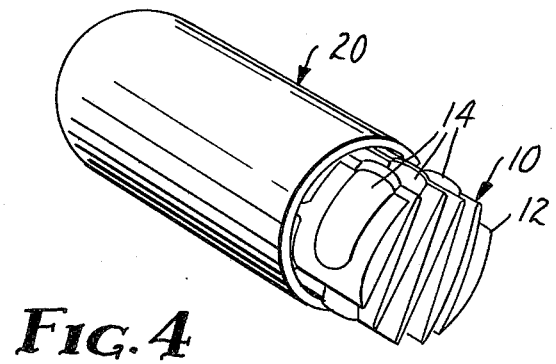
FIG. 4 is an enlarged perspective view of an open gelatin capsule having the device of the invention in pleated strip form contained therein.

FIG. 4 shows open gelatin capsule 20 having the device 10 of the present invention in pleated form contained therein.

Figure 5:
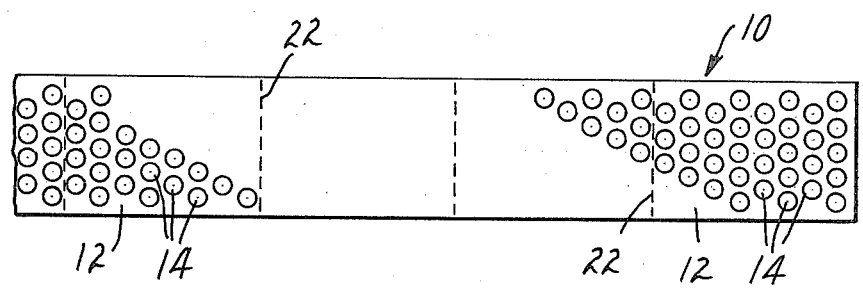
FIG. 5 is a top plan view of a modified embodiment of the invention showing perforations for division into unit dosages.

FIG. 5 shows another embodiment of the device 10 having barrier film 12, air pockets 14, and perforations 22 which are located at intervals so as to provide unit dosages.

Figure 6:
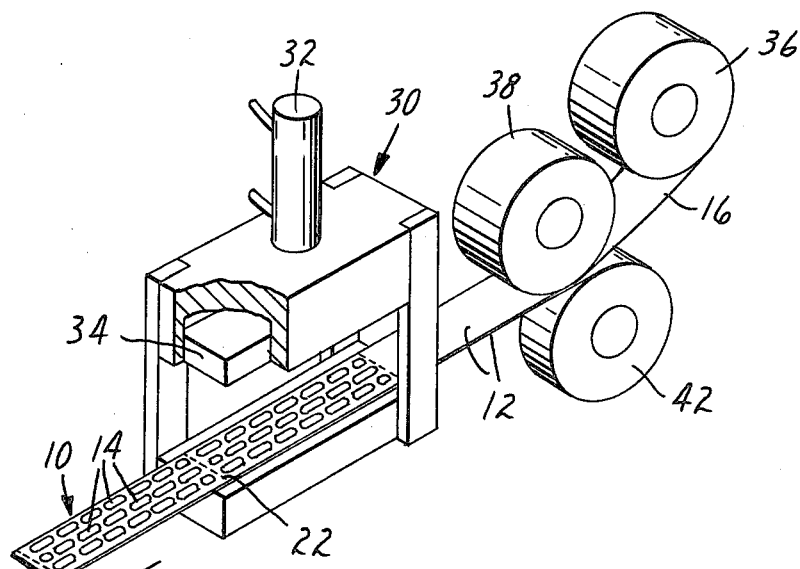
FIG. 6 is a perspective view of an apparatus for forming devices of the present invention.

FIG. 6 shows an apparatus 30 for forming the devices of the present invention. Piston 32 moves heater block 34 which has an embossing die of suitable pattern on its undersurface. Carrier film 16 unwinds from spool 36 and is overlaid on both surfaces by barrier films 12 which unwind from spools 38 and 42. Device 10, which has been embossed by the die on the lower surface of block 34 so as to provide air pockets 14 in some areas and sealing of the films in other areas, is shown moving in the direction of the arrow. Device 10 has perforations 22 therein.

The device of the present invention is an orally administered sustained release drug delivery device which is suitable for facile measurement and divisibility for prescribed medical dosage according to length and has a bulk density of less than 1.0 g/cc so as to remain buoyant in the stomach for an extended period of time during which substantially all of the medicament is released therefrom. The device of the invention can be prepared with a known amount of medicament per linear measurement. Perforations may be provided at regular intervals to provide unit dosages. When it is desirable to very accurately dispense medicament, the device of the present invention may be cut, as with a scissors for example, to the precisely predetermined length according to the prescribed dosage. The medicament device may be dispensed and administered in a compact form which extends in the stomach. For example, the device, in flexible, preferably strip form, may be rolled or folded as by pleating so as to easily fit in a gelatin capsule for oral administration. The gelatin capsule dissolves in gastric juices at physiological temperatures in a short time to allow the constrained medicament device to unroll or unfold.

The overall dimensions of the drug delivery device are about 0.004 to 0.08 cm thick with a preferred thickness between 0.02–0.03 cm, with a length dispensed according to prescribed medical dosage; a length of 14 cm is preferred. The width of the device can be from about 0.5 cm to 7.5 cm, with a preferred width of 2.1 to 6.1 cm. For veterinary use, for example, the size of the sustained release medicament device can be much larger, depending on medical and physical requirements of the animals.

The medicament delivery device of the present invention is a laminated multilayered structure comprising two polymeric films having different functions. One film is a carrier film and a second is a barrier film. The carrier film is overlaid on at least one surface thereof by an outside barrier film but is not limited to this number or arrangement of films. Polymers forming carrier and barrier films are, and remain, physiologically inert during the time of complete drug delivery.

The carrier film, of which there is at least one, is comprised of a film-forming polymer or matrix containing a medicament or active agent or drug dispersed or dissolved therein or applied thereon. By incorporating multiple carrier films in the device it is possible to vary the number and kind of medicaments released and their rates of release. Other additives such as fillers, colorants, excipients, and plasticizers may be added to the polymer by simple mixing. The polymeric material or matrix is water insoluble and capable of forming a flexible, self-supporting film when containing medicament in the concentration of up to 65 percent by weight. The matrix does not swell to any appreciable degree in water and has a softening point above 37° C., the normal physiological temperature.

Examples of polymers that may be used in the carrier film, which may comprise a plurality of layers, are ethyl cellulose, poly($\gamma$-benzyl glutamate), polyvinyl acetate, cellulose acetate phthalate, a copolymer of methyl vinyl ether with maleic anhydride, and the above polymers to which polyvinylpyrrolidone may be added. Other useful polymers and a discussion of controlled release systems in general is given in *Controlled Release Technologies; Methods, Theory, and Applications,* Vol. I, editor A. F. Kydonieus, CRC Press Inc., Boca Raton, Fla., pp. 1–14, (1980).

Table I, below, summarizes some mechanical properties and sources for polymers and polymer films that are used in the examples of this invention.

The medicament or therapeutic agent or drug can be dispersed homogeneously into the matrix, or it may be desirable to increase the concentration of the medicament from the outer wall to the interior of the carrier film to approach a zero order release behavior. Any medicament which can be given orally, and for which a sustained release action is beneficial or desirable, can be incorporated into the carrier film. The medicament can be any substance which is at least partially water-soluble and may comprise acidic, basic, neutral, or amphoteric substances. Concentration of medicament in the carrier layer can vary from 0.05 to 65 percent. The carrier may comprise a plurality of layers, generally each having at least one medicament incorporated therein, although designated carrier layers may contain no medicament.

Suitable medicaments used with the device of this invention are those mentioned in, for example, U.S. Pat. Nos. 3,625,214, 4,248,857 and 4,167,558 and in British Pat. No. 1,428,426. Some of these medicaments are, for example: acetazolamide; antacids such as calcium carbonate and aluminum hydroxide; aspirin; belladonna alkaloids; benztropine; bromocriptine; cephalothin; chloropromazine; cimetidine; dipyridamole; disopyramide; isoephedrine; isosorbide dinitrate; ephedrine; estrogens; lithium carbonate; methadone; naloxone; nitroglycerin; papavarine; penicillin; phenylpropanolamine; potassium chloride; probucol; prochlorperazine; progesterone; quinidine; terbutaline; tetracycline; theophylline; tolazoline; and trihexylphenidyl.

Plasticizers suitable for use in the carrier film of the sustained release formulations of the invention include those well known in the art of preparing coatings used in the pharmaceutical industry. Examples are acetylated monoglycerides; esters of phthalic acid such as dimethyl phthalate, dibutyl phthalate, and dioctyl phthalate; propyleneglycol; glycerol; castor oil; D-sorbitol; diacetin; triacetin; dibutyl tartarate; and the like. The preferred percentage of plasticizer varies up to 30 percent by weight with desired percentages from 1–15% of the carrier film.

An excipient is usually incorporated into the matrix of the carrier film. The excipient is a water-soluble material which gradually dissolves in the gastric juices. This gradual dissolution creates regions of porosity within the matrix. Penetration of gastric juices or water into these porous regions results in the controlled release of medicament. Excipients generally comprise from 1.0 to 30 percent by weight of the carrier film. Typical excipients are those used in the pharmaceutical industry and some examples are salt, sugar, polyvinylpyrrolidone, and polyethylene glycol (molecular weight of these latter two polymers ranges from 300–20,000).

The thickness of the carrier film is in the range of 0.001 to 0.05 cm, and preferably it is 0.015 to 0.02 cm thick.

As mentioned above, the barrier film overlays the carrier film on at least one surface. Obviously, if the medicament is dispersed homogeneously in a single carrier film, the barrier film will overlay both surfaces of the carrier film, unless it is desired to have more rapid release of medicament from one surface of the device than from the other. The purpose of the barrier film is to control the rate of release of medicament that is present in the carrier film. Another purpose of the barrier film is to control the rate of release of medicament such that the control rate profile approaches that of a zero order release profile or any other desired release rate profile. In addition, the barrier film provides buoyancy of the medicament release device in the stomach by entrapping air in small pockets between it and the carrier film.

The barrier film is comprised of at least one water-insoluble, permeable, film-forming polymer or copolymer, and optionally a water-soluble polymer or copolymer, or a mixture thereof, a plasticizer, and generally an excipient. In certain instances, the barrier film may also contain medicament. Useful water-insoluble, permeable, film-forming polymers, after leaching of the excipient or water-soluble plasticizer therefrom have a pore size, as determined by scanning electron microscopy, in the range of 0.1 to 10 microns, and preferably 0.5 to 5 microns. Portions of the surface of the outermost barrier film of the drug delivery device are fixed, sealed, or laminated onto the carrier film in such a manner that a pocket, or pockets, of air or "bubbles" are entrapped between this external film and the remainder of the drug delivery device to provide the device with buoyancy sufficient to float in the stomach (i.e., apparent specific gravity of the device is less than that of the gastric juices, which have a specific gravity of between 1.004 and 1.01) for an extended period of time during which substantially all of the medicament is released. The bulk density of the device is less than 1.0 g/cc. The barrier film has suitable flexibility and mechanical strength to allow pleating and sealing or affixing of said film onto the drug delivery device in such a manner as to become the air-entrapped or "bubble" polymer film. The barrier film comprises in the range of 17 to 60 percent by weight, and preferably 25 to 45 percent by weight, of the sustained release device.

A judicious selection of the polymers or copolymers having the required degree of permeability for forming the barrier film can dictate the rate of release of medicament from the drug delivery system. The required degree of permeability of the barrier film can be obtained by starting with a permeable polymer or by adding from 0.5 to 30 percent by weight of a water-soluble polymer to the film-forming polymer. Examples of water-insoluble, permeable film-forming polymers are ethylcellulose, polyvinyl acetate, cellulose acetate phthalate, polyesters laminated with low-density and medium-density polyethylene and copolymers of polyethylene and polyvinyl acetate. Examples of water-soluble polymers are polyvinyl pyrrolidone and hydroxypropylmethyl cellulose. TABLE I summarizes some mechanical properties and sources for some of the polymers and polymeric films that are used as examples in this invention.

TABLE I

| | Data on Polymers and Polymer Films | | |
|---|---|---|---|
| | | Physical properties | |
| | | Film tensile strength | |
| Polymer or Copolymer | Molecular Weight$^a$ or Viscosity$^{b,c}$ | Pascal (Pa) | lb./sq. in. (PSI) |
| Ethyl cellulose | 0.045–0.11 Pa · S, 45–110 cP | 5.87 × 10$^7$ | 8,520 |
| | 0.063–0.085 Pa · S, 63–85 cP (preferred for carrier film) | — | — |
| | 0.041–0.085 Pa · S, 41–85 cP (preferred for barrier film) | — | — |
| Poly(γ-benzyl glutamate)$^d$ | 50,000–100,000$^e$ | 1.65 × 10$^7$ | 2,400$^f$ |
| Copoly(ethylenevinyl-acetate)$^g$ | 50,000–100,000 | 3.8 × 10$^7$ | 5,500 |
| Cellulose acetate phthalate | 50,000–100,000 | — | — |

TABLE I-continued
Data on Polymers and Polymer Films

| | | Physical properties | |
|---|---|---|---|
| | | Film tensile strength | |
| Polymer or Copolymer | Molecular Weight[a] or Viscosity[b,c] | Pascal (Pa) | lb./sq. in. (PSI) |
| Copolymer of methyl vinyl ether - maleic anhydride[h] | High viscosity type | — | — |
| Polyethylene terephthalate polyester laminated with polyethylene[i] | 20,000 (mol. wt. of polyester) 5,000–100,000 (mol. wt. of laminated polyethylene) | $5.17 \times 10^7$ | 7,500[j] |
| | 10,000–50,000 (preferred) | $4.14 \times 10^7$ | 6,000[k] |

[a]Number average molecular weight; flow rate and pressure limit data for cellulose ester membrane materials are given in Millipore Corp. Bulletin PB085, incorporated herein by reference
[b]Viscosity reported in Pascal-second (Pa · S) and Centipoise (cP)
[c]Viscosity of Methocel ® E-15 (Dow Chemical Co.) determined as a 2% solution in water at 20° C. Viscosity of Ethocel ®-45 (Dow Chemical Co.) determined as a 5% solution in toluene-ethanol (80:20, vol/vol) at 25° C. Viscosity of Ethocel ®-70 (Dow Chemical Co.) determined as a 5% solution in toluene-ethanol (60:40, vol/vol) at 25° C.
[d]Prepared according to directions of S. B. Mitra, N. K. Patel and J. M. Anderson, Int. J. Biol. Macromolecules 1, 55 (1979)
[e]Molecular weight determined in dichloroacetic acid, see P. Doty, J. H. Bradbury and A. M. Holtzer, J. Am. Chem. Soc. 78, 947 (1956)
[f]Stress at failure reported by J. M. Anderson et al, J. Biomed. Mater. Res. Symposium, No. 3, 25 (1972)
[g]Scotchpak ® laminated copolymer (3M) heat sealable polyester film Nos. 112, 113, 115, 125
[h]Gantrez ® AN-169 copolymer (GAF)
[i]Scotchpak ® laminated copolymer (3M) Nos. 5, 6
[j]Laminated with low density polyethylene
[k]Laminated with medium density polyethylene Plasticizers suitable for use in barrier films of the invention include those well known in the art for preparing coatings used in the pharmaceutical industry and can be those plasticizers that are listed above as suitable for use in the carrier film of the invention. The percentage of plasticizer can be in the range of 0.5 to 30 percent, preferably 20 to 25 percent, by weight of the barrier film.

An excipient is usually incorporated into the film-forming polymer of the barrier film. The excipient is a water-soluble material which gradually dissolves in the gastric juices. The excipient and plasticizer (if water-soluble) allow medicament to pass through the barrier film. Typical examples of excipients are salt, sugar, and water-soluble polyvinylpyrrolidone and polyethyleneglycol mentioned above. Excipients make up from 1 to 30 percent by weight of the barrier film, with a preferred range of 20–25%.

Since the barrier film contains an excipient or a water-soluble plasticizer that, in use, dissolves in gastric juices, the film is left with opened pores. When the medicament is a solid, the barrier film preferably is of such a character as to become wetted by liquid water and thereby allows gastric juices to pass through the opened pores and come in contact with the medicament-containing carrier film. The medicament, which, to be effective has a solubility in water of at least 0.1 mg/l, dissolves in gastric juices and the resulting medicament-containing gastric juices can then pass through pores in the barrier film again and enter the stomach. Liquid medicament would even more readily enter the stomach.

The overall dimensions of the barrier film are about 0.5 cm to 7.5 cm wide, preferably 2.1 to 6.1 cm wide, with a length dispensed according to prescribed medical dosage. The most preferred overall dimensions of the barrier film are made to the same size as the carrier film, generally 14 cm long by 2.1 cm wide, with a preferred thickness between 0.002 and 0.005 cm, but the overall size is not limited to these dimensions. The preferred tensile strength of the barrier films ranges from $3.8 \times 10^7$ to $5.9 \times 10^7$ Pa (5,500 to 8,520 PSI).

The barrier film makes up 15 to 60 percent by weight of the sustained release drug device, with the preferred range being 25–45% by weight.

The barrier and carrier films may be prepared by any of the common techniques employed for the preparation of polymeric films. One method, for example, consists of dissolution of the desired polymer in a suitable solvent at ambient temperatures, followed by the addition of other ingredients such as plasticizers, excipients, drugs and other additives, to form a homogeneous dispersion or solution of high viscosity (0.1–0.5 Pa·S, 100–500 cP) followed by coating (e.g., knife coating) to a suitable thickness. Removal of solvent by heat or evaporation or a combination thereof, for example, leaves a self-supporting film.

Another method for film formation involves mixing a solid polymer with the necessary additives, e.g., plasticizers, excipients, medicinals, and extruding this mixture into a film whose thickness and shape is dictated and controlled by the dimensions of the extruding die.

The sustained release pharmaceutical delivery device is constructed from the barrier and carrier films by sealing or laminating along their edges and between air pockets, while maintaining the same perimeter to give an envelope configuration. By "envelope" is meant any complete enclosure formed by one or more sheets of the sheet material which have their edges secured together, which enclosures may be of any shape required to enclose the component. The films may be sealed or laminated together by any suitable technique, for example, by the use of heat, pressure or solvent sealing, or combinations thereof.

An apparatus, one embodiment of which is shown in FIG. 6, is provided for sealing the air entrapped, bubble-containing, or "waffle" type barrier film onto the resultant composite film of this invention. The die, which may have any pattern embossed thereon, is heated by the attached heater block, and it performs two functions. The first function is to emboss one or more of resultant sealed air sacs, bubbles or "waffle" type patterns between the top barrier film and the film, or films, under this barrier film. The second function of the embossed die is to seal together all the edges of the film composite and the areas between the air pockets to give an envelope configuration. The die may contain a row of suitably raised dimples or other suitable embossed design which leads, on the film composite, to a row of perforations, see FIGS. 5 and 6, or other marked interval design, suitable for detaching, tearing or cutting the device of this invention.

A second means for simply sealing films together involves the use of a jaw-type sealer (robot Model RTP-F sealer, Pack-Rite Machine Division, Wrapping Machine Company, Franksville, WI).

In all sealing operations, a protective film, e.g., a polyester liner 0.5 mil to 1 mil (0.001 to 0.002 cm) thick, is used on the embossing die to prevent the sealed medicament delivery device of this invention from adhering to the sealing apparatus used.

Heat sealing temperature ranges for barrier films of polyester/polyethylene are 149°–204° C. and those for the other films are 135°–149° C., with a time duration of 0.2–2 seconds, and a preferred time of 0.75–1 second, at pressures of 0.01–0.06 Pa·S (10–60 PSI), with preferred pressures of 0.012–0.015 Pa·S (12–15 PSI).

A limiting condition for buoyancy of laminated composite film structures of this invention is that the overall apparent density must be less than that of the gastric juice, i.e., less than 1.0 g/cc. Theophylline-containing composite film structures of this invention having the configuration shown in FIG. 1 were prepared having a variety of lengths and widths. Theophylline-containing composite films, which were similarly laminated but had no air pockets, served as controls. They were also prepared having the same variety of lengths and widths as shown in TABLE II. The surface area and weight per unit area for all the composite structures were essentially the same, yet the apparent density of the controls was greater than that of the gastric juice and greater than that of the sustained release device of this invention, wherein the apparent density is less than that of gastric juice. Furthermore, the control and the device of this invention had the same type of wetting characteristics as determined by contact angle measurements; hence, wetting was not a factor in flotation behavior.

TABLE II

Buoyancy Studies of a Theophylline-Containing Sustained Release Device[a]

| Laminated composite film type[b] | Composite Measurements | | |
|---|---|---|---|
| | Length × Width (cm$^2$) | Weight/unit area (g/cm$^2$) | Apparent density[c] (g/cm$^3$) |
| C | 2.1 × 14 | 0.0233 | 1.21 |
| SRD | 2.1 × 14 | 0.0241 | 0.62 |
| C | 3.1 × 9.1 | 0.0235 | 1.18 |
| SRD | 3.1 × 9.1 | 0.0232 | 0.62 |
| C | 4.2 × 7.0 | 0.0234 | 1.24 |
| SRD | 4.2 × 7.0 | 0.0231 | 0.64 |
| C | 5.1 × 5.1 | 0.0230 | 1.24 |
| SRD | 5.1 × 5.1 | 0.0234 | 0.62 |
| C | 6.1 × 4.7 | 0.0220 | 1.23 |
| SRD | 6.1 × 4.7 | 0.0226 | 0.66 |

[a] In all cases, the thickness of the carrier film is 6 mil (0.015 cm) and that of the barrier films is 1 mil each (0.002 cm)
[b] C = control; SRD = sustained release device of the invention
[c] Determined with a pycnometer; density of gastric juices = 1.004–1.01

The data of TABLE II show that the devices of the present invention with air pockets entrapped therein had apparent densities less than 1.0 g/cc, wherein similar devices without entrapped air had apparent densities substantially higher than 1.0 g/cc.

The rate of release of medicaments from the sustained medicament release device of this invention was followed by in vitro and in vivo techniques. For example, the in vitro release behavior of theophylline from the medicament containing films of the device was studied using a United States Pharmacopeia No. 2 Dissolution Apparatus (United States Pharmacopeia, Mack Publishing Co., Easton, PA 18042, 20th Revision, 1980, p. 959) wherein the level of the drug released into a non-pepsin containing artificial gastric juice was monitored by ultraviolet spectroscopy at 270.5 nm. Results are shown in TABLE III below.

TABLE III

In Vitro Release of Theophylline into Artificial Gastric Juice

| Time (hours) | % Drug released |
|---|---|
| 1 | 11 |
| 2 | 17 |
| 3 | 23 |
| 4 | 29 |
| 5 | 35 |
| 6 | 41 |
| 7 | 47 |
| 8 | 52 |
| 9 | 59 |
| 10 | 65 |
| 11 | 71 |
| 12 | 77 |
| 13 | 83 |
| 14 | 88 |
| 15 | 93 |
| 16 | 96 |
| 17 | 99 |
| 18 | 100 |

The release rate profile presented numerically in Table III (see Example 10 for preparation of device) shows that the rate of release of theophylline approaches a zero order release rate, i.e., a constant amount of medicament is released.

In vivo gastric studies to determine gastric residence time of a device of this invention were run using a radio-opaquing technique on beagle dogs. For example, a barrier film coated with radio-opaque barium sulfate, within a theophylline-containing controlled release device, was pleated and placed inside a gelatin capsule. It was then administered to beagle dogs according to a suitable empirical protocol described below. Non-disintegrating radio-opaque tablets containing a compressed, tabletted mixture of lead solder wire with ethyl cellulose served as controls. The dogs were examined using X-rays for many hours thereafter to follow the fate of the administered materials. The data are given in TABLE IV below.

The in vivo gastric studies, which were designed to minimize experimental variations, followed the five step empirical protocol:

1. Food and water was available to the test animals before and during the experiment.
2. The capsule containing the film was administered with 50 ml of water.
3. X-rays were taken immediately after administering the capsule or tablet and then every hour thereafter.
4. The experimental dog was placed in a sling during the time the X-ray was being taken. At all other times, the dog was kept in the dog-run.
5. The film device of the present invention was administered to the dog and on the next day a control tablet was administered to the same dog.

TABLE IV

Gastric Residence Times of Samples in Beagle Dogs

| | Gastric residence time (hours) | |
|---|---|---|
| Experiment No. | Sustained release device | Control |
| 1 | 7 | —[b] |
| 2 | 5 | 1 |

TABLE IV-continued
Gastric Residence Times of Samples in Beagle Dogs

| Experiment No. | Gastric residence time (hours) Sustained release device | Control |
|---|---|---|
| 3 | 4 | 1 |
| 4 | 8[a] | 6 |
| 5 | 7 | 4 |
| 6 | 8[a] | 1 |
| 7 | 8 | 2 |
| 8 | 6 | 1 |
| 9 | 5 | 2 |
| 10 | 4 | 4 |
| 11 | 6 | 1 |
| 12 | 5 | 3 |
| 13 | 8[a] | 2 |
| 14 | 7 | 4 |
| 15 | 8 | —[b] |
| 16 | 6 | 2.5 |
| 17 | —[b] | 1 |
| 18 | 8[a] | 2 |
| 19 | 7 | 5 |
| Mean Value | 6.5 | 2.5 |

[a]Sustained release device still present in the stomach after eight hours. Experiment discontinued at this time.
[b]Not determined.

Table IV indicates that, within experimental variations, the controlled release device did open or unfold in the stomach of the beagle and the gastric residence time (mean value of 6.5 hours) of the device of this invention was much longer than that of the control (mean value of 2.5 hours).

Objects and advantages of this invention are further illustrated by the following examples, but the particular materials and amounts thereof recited in these examples, as well as other conditions and details, should not be construed to unduly limit this invention. Parts and percentages are by weight unless otherwise indicated, and temperatures are in degrees centigrade.

In the examples that follow, solutions, dispersions and other materials used to construct articles of the present invention were selected from the articles in Table V.

TABLE V
Formulations for Articles of the Invention

| Formulation number | Materials | Weight (g) | Volume (ml) | Instructions |
|---|---|---|---|---|
| I | Ethocel-70 | 75 | — | dissolve solid |
|  | chloroform | — | 375 | in liquid |
|  | methanol | — | 125 | mixture |
| II | Ethocel-45 | 75 | — | dissolve solid |
|  | chloroform | — | 375 | in liquid |
|  | methanol | — | 125 | mixture |
| III | Methocel E-15 | 75 | — | dissolve solid |
|  | chloroform | — | 450 | in liquid |
|  | methanol | — | 150 | mixture |
| IV | formulation I | 20.4 | — | mix |
|  | formulation II | 20.4 | — |  |
|  | Myvacet ® 9-40 (Eastman) | 2.0 | — |  |
|  | polyethylene glycol, PEG 380 (Union Carbide) | 2.4 | — |  |
| V | formulation IV | 5 | — | mix with air- |
|  | formulation III | 2 | — | driven motor |
| VI | formulation I | 85.7 | — | [a] |
|  | formulation II | 85.7 | — |  |
|  | Myvacet 9-40 | 8.4 | — |  |
|  | salt, powdered | 10.1 | — |  |
| VII | formulation I | 21.7 | — | [a] |
|  | PEG 380 | 1.16 | — |  |
|  | Myvacet 9-40 | 1.09 | — |  |
|  | quinidine gluconate 51.7%[b] | 4.80 | — |  |
| VIII | formulation I | 21.7 | — | [a] |
|  | PEG 380 | 1.6 | — |  |
|  | Myvacet 9-40 | 1.6 | — |  |
|  | quinidine gluconate 40%[b] | 3.6 | — |  |
| IX | formulation I | 21.7 | — | [a] |
|  | PEG 380 | 1.16 | — |  |
|  | Myvacet 9-40 | 1.09 | — |  |
|  | quinidine gluconate 18%[b] | 1.2 | — |  |
| X | formulation I | 217.6 | — | [a] |
|  | PEG 380 | 11.6 | — |  |
|  | Myvacet 9-40 | 10.9 | — |  |
|  | theophylline | 48.0 | — |  |
| XI | formulation VI | 40 | — | mix |
|  | formulation III | 16 | — |  |
| XII | formulation I | 27.2 | — | mix and |
|  | PEG 380 | 1.4 | — | homogenize[a] |
|  | Myvacet 9-40 | 1.4 | — |  |
|  | acetic acid | — | 8 |  |
|  | theophylline | 6.0 | — |  |
| XIII | formulation I | 6.8 | — | mix |
|  | PEG 380 | — | 0.35 |  |
|  | Myvacet 9-40 | — | 0.35 |  |
| XIV | formulation I | 6.1 | — | mix |
|  | formulation II | 0.7 | — |  |
|  | PEG 380 | — | 0.35 |  |

TABLE V-continued

| Formulation number | Materials | Weight (g) | Volume (ml) | Instructions |
|---|---|---|---|---|
| | Myvacet 9-40 | — | 0.35 | |
| XV | formulation I | 4.7 | — | mix |
| | formulation II | 2.1 | — | |
| | PEG 380 | — | 0.35 | |
| | Myvacet 9-40 | — | 0.35 | |
| XVI | formulation I | 2.1 | — | mix |
| | formulation II | 4.7 | — | |
| | PEG 380 | — | 0.35 | |
| | Myvacet 9-40 | — | 0.35 | |
| XVII | formulation I | 54.4 | — | mix and homogen- |
| | PEG 380 | 3.0 | — | ize[a] (Brookfield |
| | Myvacet 9-40 | 3.0 | — | viscosity: |
| | acetic acid | — | 16 | $\eta = 3{,}000$ cP, |
| | theophylline | 12.0 | — | 3 Pa · S) |
| XVIII | polyvinyl acetate | 20 | — | dissolve using |
| | acetone | — | 100 | high-speed stirring |
| XIX | formulation XVIII | 10 | — | mix and |
| | theophylline | 2 | — | homogenize[a] |
| XX | Gantrez AN-169 | 50 | — | dissolve |
| | acetone | — | 200 | |
| XXI | formulation XX | 7.2 | — | mix and |
| | PEG 380 | 3.0 | — | homogenize[a] |
| | theophylline | 10 | — | |
| XXII | cellulose acetate phthalate | 25 | — | dissolve |
| | acetone | — | 100 | |
| XXIII | formulation XXII | 4.8 | — | mix |
| | PEG 380 | 2.6 | — | |
| | Myvacet 9-40 | 2.4 | — | |
| XXIV | formulation XXII | 4.8 | — | mix and |
| | PEG 380 | 2.6 | — | homogenize[a] |
| | Myvacet 9-40 | 2.4 | — | |
| | theophylline | 10.2 | — | |
| XXV | formulation I | 21.7 | — | mix and |
| | PEG 380 | 1.6 | — | homogenize[a] |
| | Myvacet 9-40 | 1.6 | — | |
| | theophylline | 3.6 | — | |
| XXVI | formulation I | 21.7 | — | mix and |
| | PEG 380 | 1.6 | — | homogenize[a] |
| | Myvacet 9-40 | 1.6 | — | |
| | theophylline | 1.2 | — | |
| XXVII | formulation I | 85.7 | — | [a] |
| | formulation II | 85.7 | — | |
| | Myvacet 9-40 | 8.4 | — | |
| | sugar, powdered | 10.1 | — | |
| XXVIII | formulation XXVII | 40 | — | [a] |
| | formulation III | 16 | — | |

[a] Add components to liquid, or liquids, and mix by means of high-speed mechanical stirring. Dispersions are homogenized using hand-held homogenizer and then roll-milled for 0.5 hour at 250 rpm before use in coating films.
[b] Percent by weight in the film after removal of solvent.

EXAMPLES

Example 1—preparation of a theophylline-containing sustained release device

A carrier film was prepared by knife coating 25 g of formulation X (TABLE V) onto a 4 mil (0.01 cm) supporting polyester (polyethylene terephthalate, 3 M) sheet. The gap between the knife of the coater and the polyester film supported on the stainless steel bed of the coater was 15 mil (0.038 cm). The cast film was allowed to air dry for several hours and then dried in vacuum for one day. The supporting polyester film was peeled away from the dry theophylline-containing film whose thickness was 6 mils (0.015 cm). This carrier film was cut into a 2.1 cm×14 cm rectangular strip which weighed 0.5 g.

A barrier film was prepared by knife coating 20.4 g of formulation IV (TABLE V) onto the supporting polyester film mentioned above with the knife gap set at 4 mils (0.01 cm). This film was allowed to air dry for several hours and then dried in vacuum for one day. The polyester backing film was peeled from the dried barrier film whose thickness was 1 mil (0.0025 cm). Two 2.1 cm×14 cm rectangular barrier film strips, cut from the above dried barrier film, were fitted on each side of the resultant middle theophylline-containing carrier film strip so as to entrap air and maintain the same perimeter in an envelope configuration. The peripheral edges of the three strips of film were heat sealed under pressure at 135° C. at $9.65 \times 10^5$ Pa (140 PSI) for 0.75 second. This medicament device was pleated to fit inside a size zero gelatin capsule.

The release rate profile of the sustained release device of this example was measured in vitro at 37° C. using a one liter United States Pharmacopeia (USP) No. 2 Dissolution Apparatus (mfg. by Hanson Research Corp., Northridge, CA) containing 900 ml of 0.1 N-hydrochloric acid. A Teflon ® (DuPont) screen was placed 2.5 cm from the bottom of the dissolution flask. The Teflon coated paddle, kept just above the screen, rotated at 50 rpm.

The above capsule containing the medicament device was weighted with paper clips and placed inside the dissolution flask. In about ten minutes, the capsule dissolved and the medicament-containing device floated but was prevented from contacting the paddle by the Teflon screen. The dissolution medium was constantly monitored by ultraviolet spectrophotometry at 270.5 nm to measure the quantity of theophylline released into the dilute acid solution by the medicament device. The percent drug released versus time is tabulated in Table VI below.

Examples 2-6

The following is a model procedure for specific Examples 2-6. In vitro results are summarized in Table VI below.

The carrier films of Examples 2-4 were prepared by knife coating formulation XII (Table V) onto a 4 mil (0.01 cm) polyester sheet using a 25 mil (0.064 cm) knife coating gap. The resultant film was dried to leave a film 6 mil (0.015 cm) thick. The carrier film of Example 5 was prepared as described above with the exception that formulation XVII (Table V) was used in place of formulation XII. The carrier film for Example 6 was that described in Example 1.

The barrier films of Examples 2-6 were prepared by knife coating the specified formulation indicated in Table VII below according to the directions for preparing 1 mil (0.0025 cm) thick barrier films as detailed in Example 1.

The suitable number of 2.1 cm×14 cm rectangular strips were cut from the respective dry barrier and carrier films and assembled and heat sealed as described in Example 1 to afford the sustained release medicaments whose release rate profiles, presented numerically, are given in Table VI below.

TABLE VI

In Vitro Release of Theophylline for Examples 1-6

| Time (hours) | % Drug released | | | | | |
|---|---|---|---|---|---|---|
| | Ex. 1 | Ex. 2 | Ex. 3 | Ex. 4 | Ex. 5 | Ex. 6 |
| 2 | 11 | 1 | 2 | 3 | 25 | 22 |
| 4 | 21 | 4 | 4 | 7 | 52 | 45 |
| 6 | 30 | 6 | 7 | 11 | 69 | 65 |
| 8 | 37 | 9 | 11 | 15 | 80 | 81 |
| 10 | 44 | 11 | 14 | 20 | 86 | 92 |
| 12 | 50 | 13 | 16 | 24 | 90 | 97 |
| 14 | 56 | 15 | 19 | 28 | 94 | 100 |
| 16 | 60 | 18 | 21 | 32 | 97 | |
| 18 | 66 | 20 | 25 | 37 | 98 | |
| 20 | 70 | 23 | 27 | 40 | 99 | |
| 22 | 74 | 25 | 31 | 45 | 100 | |
| 24 | 79 | 27 | 33 | 49 | | |
| 26 | 83 | 30 | 36 | 54 | | |
| 28 | 87 | 32 | 40 | 58 | | |
| 30 | 93 | 34 | 43 | 62 | | |
| 32 | 95 | 37 | 46 | 66 | | |
| 34 | 99 | 40 | 49 | 70 | | |
| 36 | 100 | 43 | 52 | 73 | | |
| 38 | | 44 | 54 | 77 | | |
| 40 | | 47 | | | | |

TABLE VII

Barrier Film Formulations for Sustained Release Medicaments

| Ex. No. | Formulation used for barrier film[a] |
|---|---|
| 2 | XIII |
| 3 | XIV |
| 4 | XV |
| 5 | XVI |

TABLE VII-continued

Barrier Film Formulations for Sustained Release Medicaments

| Ex. No. | Formulation used for barrier film[a] |
|---|---|
| 6 | V |

[a]Formulation number refers to that in Table V. In vitro release rate profiles are determined as described in Example 1 (see Table VI for data).

Examples 7-9

The following is a model procedure for Examples 7-9 with in vitro results summarized in Table IX below.

The carrier films of Examples 7-9 were prepared by knife coating the specified formulation for carrier films indicated in Table VIII onto a 4 mil (0.01 cm) polyester sheet using a 24 mil (0.06 cm) knife coating gap. The resultant film was dried to leave a film having a thickness as reported in Table VIII.

The barrier films of Examples 7-9 were prepared as described in Example 1 using the corresponding specified formulation for barrier films indicated in Table VIII. The thickness of these films are also given in Table VIII.

Strips measuring 2.1 cm×14 cm rectangular were cut from these corresponding barrier and carrier films and assembled and heat sealed as described in Example 1 to give the sustained release medicaments having release rate profiles which are numerically presented in Table IX below.

TABLE VIII

Films for Sustained Release Medicaments of Examples 7-9

| | Carrier Film[a] | | Barrier Film[a] | |
|---|---|---|---|---|
| Ex. No. | Formulation | Thickness [mil (cm)] | Formulation | Thickness [mil (cm)] |
| 7 | XIX | 8 (0.020) | V | 1 (0.002) |
| 8 | XXI | 9.5 (0.024) | V | 1 (0.002) |
| 9 | XXIV | 8 (0.020) | XXII | 1 (0.002) |

[a]Formulation number refers to that in Table V; thickness is reported for dry film. In vitro release rate profiles were determined as described in Example 1 (see Table IX for data).

TABLE IX

In Vitro Release of Theophylline for Examples 7-9

| Time (hours) | % Drug Released | | |
|---|---|---|---|
| | Ex. 7 | Ex. 8 | Ex. 9 |
| 1 | 24 | 12 | 12 |
| 2 | 41 | 26 | 21 |
| 3 | 55 | 42 | 29 |
| 4 | 67 | 59 | 35 |
| 5 | 76 | 75 | 41 |
| 6 | 83 | 85 | 47 |
| 7 | 87 | 89 | 52 |
| 8 | 90 | 91 | 57 |
| 9 | 92 | 92 | 61 |
| 10 | 93 | 93 | 65 |
| 11 | 94 | 93 | 69 |
| 12 | 95 | 94 | 72 |
| 13 | 95 | 95 | 75 |
| 14 | | | 78 |
| 15 | | | 80 |
| 16 | | | 83 |
| 17 | | | 85 |
| 18 | | | 86 |

Example 10—preparation and fabrication of a multi-laminated sustained release medicament device of this invention Carrier films containing 18%, 40% and 51% theophylline, respectively, were prepared according to the directions in Example 1 using the formulations given in Table X.

TABLE X

Preparation of Carrier Films for Example 10

| Carrier Film No. | Thickness[a] [mil (cm)] | % Theophylline | Formulation[b] |
|---|---|---|---|
| A | 1 (0.002) | 18 | XXVI |
| B | 2.7 (0.007) | 40 | XXV |
| C | 3 (0.008) | 51 | X |

[a] Film thickness of dry film
[b] Formulation number refers to that in Table V

Using carrier films A, B and C, a five-layered carrier film composite was fabricated such that carrier film C was sandwiched between two carrier films B, which were in turn sandwiched between two outer carrier films A. In construction, each carrier film was sequentially pressure laminated at about 135° C. under a pressure of 14 PSI ($9.6 \times 10^4$ Pa) for about 0.75 second to form the resultant 8 mil (0.02 cm) thick carrier film composite. It was cut into a 2.1 cm × 14 cm rectangular strip.

The barrier film, prepared as described in Example 6, was made to envelope the carrier film composite. The four sides of the resulting barrier film envelope were heated sealed at the boundaries onto the carrier film under the above stated conditions such that air was entrapped between the two larger outer surfaces of the carrier and barrier films. This resultant sustained release medicament had a release rate profile, presented numerically, which is presented in Table III above.

Examples 11–16

The following is a model procedure for specific Examples 11–16. Formulations used are summarized in Table XI below.

The carrier films of Examples 11–14 were prepared as described in Example 1. The carrier films for Examples 15 and 16 were similarly prepared by knife coating formulation VII (Table V) to give a resultant dry carrier film 7 mils (0.017 cm) thick. The carrier films were cut into rectangular strips (2.1 cm × 14 cm).

The barrier films were cast by knife coating the specified formulation for barrier films indicated in Table XI at a knife coating thickness of 5 mils (0.01 cm) according to the direction in Example 1. The dry barrier films were 1 mil (0.002 cm) thick. The sustained release medicament device was assembled from the central carrier film and two outer barrier films as detailed in Example 1 and release profiles, presented numerically, are given in Table XII below.

TABLE XI

Preparation of Barrier Films for Examples 11–16

| Ex. No. | Formulation used for barrier film[a] |
|---|---|
| 11 | VI |
| 12 | XI |
| 13 | XXVII |
| 14 | XXVIII |
| 15 | V |
| 16 | IV |

[a] Formulation number refers to that in Table V. In vitro release rate profiles are determined as described in Example 1 (see Table XII for data).

Example 17—a multilayered drug release device containing quinidine gluconate

A carrier film composite was prepared in five sequential steps. Formulation IX (Table V) was knife coated onto a 4 mil (0.01 cm) polyester sheet according to the directions in Example 1 to yield on drying a 1 mil (0.002 cm) thick carrier film. Onto this film was knife coated Formulation VIII (Table V) which on drying gave a film of total thickness 3 mils (0.008 cm). On top of this composite was coated a third formulation, Formulation VII, which on drying gave a film having a total thickness of 5 mils (0.013 cm). This was followed by a coating of Formulation VII and then a coating of Formulation IX in the usual manner to give a film with total thickness of 8 mils (0.02 cm). The resulting composite was cut into a rectangular (2.1 cm × 14 cm) sheet. It was enveloped according to the directions in Example 10 by a barrier film prepared as described in Example 2. Medicament release profile presented numerically for this device is given in Table XII.

TABLE XII

In Vitro Release of Drugs for Examples 11–17

| Time (hours) | % Drug Released[a] | | | | | | |
|---|---|---|---|---|---|---|---|
| | Ex. 11 | Ex. 12 | Ex. 13 | Ex. 14 | Ex. 15 | Ex. 16 | Ex. 17 |
| 1 | 6 | 10 | 8 | 14 | 14 | 3 | 7 |
| 2 | 13 | 21 | 16 | 28 | 33 | 8 | 12 |
| 3 | 19 | 31 | 23 | 42 | 49 | 12 | 20 |
| 4 | 25 | 42 | 30 | 56 | 60 | 17 | 26 |
| 5 | 31 | 51 | 36 | 68 | 69 | 23 | 32 |
| 6 | 36 | 60 | 42 | 77 | 76 | 27 | 39 |
| 7 | 42 | 68 | 47 | 85 | 80 | 30 | 46 |
| 8 | 46 | 75 | 52 | 90 | 84 | 34 | 52 |
| 9 | 51 | 81 | 57 | 93 | 88 | 38 | 59 |
| 10 | 55 | 86 | 61 | 95 | 91 | 42 | 65 |
| 11 | 60 | 90 | 66 | 96 | 93 | 45 | 71 |
| 12 | 64 | 92 | 70 | 98 | 95 | 48 | 78 |
| 13 | 69 | 94 | 75 | 99 | 96 | 51 | 83 |
| 14 | 73 | 95 | 79 | | 98 | 53 | 90 |
| 15 | 77 | 98 | 83 | | 98 | 56 | 94 |
| 16 | 82 | 98 | 86 | | 100 | 58 | 97 |
| 17 | 85 | 99 | 89 | | | 60 | 99 |
| 18 | 89 | 99 | 92 | | | 63 | 100 |
| 19 | 91 | 99 | 95 | | | 65 | |
| 20 | 93 | 100 | 97 | | | 67 | |
| 21 | 95 | | 98 | | | 69 | |
| 22 | 98 | | 99 | | | 70 | |

[a] Theophylline is the drug in Examples 11–14; quinidine gluconate is the drug in Examples 15–17

I claim:

1. A flexible, sheet-like, sustained release medicament device for orally administering a predetermined selective dose of a medicament, which device is of a multilayer composite construction comprising
   (a) at least one dry, self-supporting carrier film comprising at least one water-insoluble polymer matrix and containing medicament dispersed or dissolved therein, and
   (b) at least one barrier film overlaying said carrier film on at least one surface thereof and sealed to said carrier film along its periphery and in such a way as to entrap a plurality of small pockets of air between said carrier and barrier films, said barrier film comprising at least one water-insoluble and water- and medicament-permeable polymer or copolymer, said multilayer composite construction having a bulk density of less than 1.0 g/cc and being facilely divisible into any desired length.

2. The device according to claim 1 wherein said barrier film comprises in the range of 17 to 60 percent of the total weight of said device.

3. The device according to claim 2 wherein said barrier film comprises in the range of 25 to 45 percent of the total weight of said device.

4. The device according to claim 1 wherein said device has a thickness in the range of 0.004 to 0.08 cm.

5. The device according to claim 4 wherein said device has a thickness in the range of 0.02 to 0.03 cm.

6. The device according to claim 1 wherein said device is a strip having a width in the range of 0.5 to 7.5 cm.

7. The device according to claim 1 wherein said device is a strip having a width of 2.1 cm and a length of 14 cm.

8. The device according to claim 1 wherein said carrier film further comprises up to 65 percent by weight of at least one medicament.

9. The device according to claim 1 wherein said carrier film further comprises in the range of 0.5 to 30 percent by weight of a plasticizer.

10. The device according to claim 9 wherein said carrier film further comprises in the range of 1 to 15 percent by weight of a plasticizer.

11. The device according to claim 1 wherein said carrier film further comprises in the range of 1.0 to 30 weight percent of an excipient.

12. The device according to claim 1 wherein said barrier film comprises in the range of 0.5 to 30 percent by weight of a water-soluble polymer.

13. The device according to claim 1 wherein said barrier film further comprises in the range of 0.5 to 30 weight percent of a plasticizer.

14. The device according to claim 13 wherein said barrier film further comprises in the range of 20 to 25 weight percent of a plasticizer.

15. The device according to claim 1 wherein said barrier film further comprises in the range of 1.0 to 30 percent by weight of an excipient.

16. The device according to claim 15 wherein said excipient is present in the range of 20 to 25 percent by weight of the barrier film.

17. The device according to claim 1 wherein said barrier film has a thickness in the range of 0.002 to 0.005 cm.

18. The device according to claim 1 wherein said barrier film has a tensile strength in the range of $3.8 \times 10^7$ to $5.9 \times 10^7$ Pa.

19. The device according to claim 1 further comprising perforations at intervals along said device to provide unit dosages.

20. A method for prepring a flexible, sheet-like, sustained release medicament device for orally administering a predetermined selective dose of a medicament, which device is a multilayer composite construction having a bulk density of less than 1.0 g/cc and being facilely divisible into any desired length, said method comprising the steps:

(a) providing at least one dry, self-supporting carrier film comprising at least one water-insoluble polymer matrix and containing medicament dispersed or dissolved therein, (b) overlaying said carrier-film on at least one surface thereof with at least one barrier film comprising at least one water-insoluble and water- and medicament-permeable polymer or copolymer, and (c) sealing said barrier-film to said carrier film in such a way as to entrap a plurality of small pockets of air between said films.

* * * * *